United States Patent
Freiburger et al.

(10) Patent No.: US 9,239,373 B2
(45) Date of Patent: Jan. 19, 2016

(54) ADAPTIVE IMAGE OPTIMIZATION IN INDUCED WAVE ULTRASOUND IMAGING

(75) Inventors: Paul Donald Freiburger, Seattle, WA (US); Liexiang Fan, Sammamish, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 111 days.

(21) Appl. No.: 13/298,182

(22) Filed: Nov. 16, 2011

(65) Prior Publication Data

US 2013/0123630 A1    May 16, 2013

(51) Int. Cl.
*A61B 8/00* (2006.01)
*G01S 7/52* (2006.01)
*A61B 8/08* (2006.01)

(52) U.S. Cl.
CPC ............ *G01S 7/52042* (2013.01); *A61B 8/485* (2013.01); *A61B 8/5269* (2013.01); *A61B 8/5292* (2013.01); *G01S 7/52046* (2013.01); *A61B 8/469* (2013.01); *G01S 7/52085* (2013.01)

(58) Field of Classification Search
None
See application file for complete search history.

(56) References Cited

U.S. PATENT DOCUMENTS

| | | | |
|---|---|---|---|
| 5,251,645 A | 10/1993 | Fenn | |
| 5,606,971 A * | 3/1997 | Sarvazyan | 600/438 |
| 5,810,731 A * | 9/1998 | Sarvazyan et al. | 600/438 |
| 6,511,427 B1 * | 1/2003 | Sliwa et al. | 600/438 |
| 6,645,144 B1 * | 11/2003 | Wen et al. | 600/437 |
| 6,764,448 B2 * | 7/2004 | Trahey et al. | 600/437 |
| 6,770,033 B1 * | 8/2004 | Fink et al. | 600/443 |
| 7,022,077 B2 * | 4/2006 | Mourad et al. | 600/449 |
| 7,175,599 B2 * | 2/2007 | Hynynen et al. | 600/443 |
| 7,252,004 B2 * | 8/2007 | Fink et al. | 73/597 |
| 7,344,509 B2 * | 3/2008 | Hynynen et al. | 601/3 |
| 7,731,661 B2 * | 6/2010 | Salcudean et al. | 600/437 |
| 8,038,616 B2 * | 10/2011 | Angelsen et al. | 600/437 |
| 8,187,187 B2 * | 5/2012 | Fan et al. | 600/438 |
| 8,225,666 B2 * | 7/2012 | McAleavey | 73/602 |
| 8,267,865 B2 * | 9/2012 | Hoyt et al. | 600/438 |
| 8,287,456 B2 * | 10/2012 | Daigle | 600/437 |
| 8,428,687 B2 * | 4/2013 | Konofagou et al. | 600/407 |
| 8,469,891 B2 * | 6/2013 | Maleke et al. | 600/438 |
| 8,647,276 B2 * | 2/2014 | Tabaru et al. | 600/449 |
| 8,801,614 B2 * | 8/2014 | Hsu et al. | 600/438 |
| 8,932,237 B2 * | 1/2015 | Vitek et al. | 601/2 |
| 8,961,418 B2 * | 2/2015 | Fan | 600/438 |
| 8,968,205 B2 * | 3/2015 | Zeng et al. | 600/459 |
| 8,992,426 B2 * | 3/2015 | Fan et al. | 600/437 |
| 2004/0167403 A1 * | 8/2004 | Nightingale et al. | 600/437 |
| 2004/0210134 A1 * | 10/2004 | Hynynen et al. | 600/439 |
| 2004/0210135 A1 * | 10/2004 | Hynynen et al. | 600/439 |
| 2004/0225215 A1 * | 11/2004 | Querleux et al. | 600/437 |
| 2005/0119568 A1 * | 6/2005 | Salcudean et al. | 600/437 |
| 2006/0173313 A1 | 8/2006 | Liu et al. | |

(Continued)

OTHER PUBLICATIONS

Marsac, L. et al., "Adaptive focusing of transcranial therapeutic ultrasound using MR Acoustic Radiation Force Imaging in a clinical environment," *IEEE Xplore, Digital Library*, Ultrasonics Symposium (IUS), 2010 IEEE International. (abstract only).

(Continued)

*Primary Examiner* — Nicholas Evoy (57) ABSTRACT

Adaptive image optimization is provided in induced wave ultrasound imaging. The values for various transmit and receive parameters may be set adaptively. Based on feedback from use with a given patient, the values are set to better optimize signal-to-noise ratio, off-time, tracking accuracy or other consideration. Transmit frequency, F-number, line spacing, tracking pulse repetition frequency, line sampling count, and/or push pulse amplitude values may adapt.

17 Claims, 2 Drawing Sheets

(56) References Cited

U.S. PATENT DOCUMENTS

| | | | |
|---|---|---|---|
| 2009/0304246 A1* | 12/2009 | Walker et al. | 382/128 |
| 2010/0016718 A1* | 1/2010 | Fan et al. | 600/438 |
| 2010/0016719 A1* | 1/2010 | Freiburger et al. | 600/443 |
| 2010/0280373 A1* | 11/2010 | Fan et al. | 600/439 |
| 2010/0317971 A1* | 12/2010 | Fan et al. | 600/439 |
| 2011/0184287 A1* | 7/2011 | McAleavey | 600/438 |
| 2011/0270136 A1* | 11/2011 | Vitek et al. | 601/2 |
| 2011/0275963 A1* | 11/2011 | Wagner et al. | 601/2 |

OTHER PUBLICATIONS

Larrat, B. et al., "Energy-based adaptive focusing: Optimal ultrasonic focusing using magnetic resonance guidance," *IEEE Xplore, Digital Library*, Ultrasonics Symposium (IUS), 2009 IEEE International. (abstract only).

Nightingale, Kathryn, et al., "On the feasibility of remote palpation using acoustic radiation force", The Journal of the Acoustical Society of America, American Institute of Physics for the Acoustical Society of America, New York, NY, US, vol. 110, No. 1, Jul. 31, 2001, pp. 625-634, XP012002408.

Palmeri, M. L., et al., "Acoustic radiation force-based elasticity imaging methods", Ultrasound in Medicine & Biology, vol. 35, No. 11, Jun. 8, 2011, pp. 1-12, XP055135439.

Search Report and Written Opinion dated Aug. 20, 2014 from counterpart French application No. 12 60876, 9 pages total.

* cited by examiner

ADAPTIVE IMAGE OPTIMIZATION IN INDUCED WAVE ULTRASOUND IMAGING

BACKGROUND

The present embodiments relate to induced wave ultrasound imaging. In particular, ultrasound shear wave and/or acoustic radiation force imaging may be improved.

Acoustic radiation force imaging (ARFI) generates a longitudinal wave in tissue with acoustic energy. Characteristics of the wave propagation indicate tissue characteristics, such as elasticity. Similarly, shear wave velocity information may be useful for diagnosis. Rather than a longitudinal wave, the shear wave generated by acoustic energy is monitored. Shear wave information may indicate tissue characteristics in addition to acoustic impedance (e.g., B-mode) and Doppler (e.g., flow mode) imaging. However, acoustic wave induced imaging is hampered by limitations on transducer and tissue heating, causing down-time during imaging. These acoustic wave induced imaging techniques may provide less information than is available due to configuration limitations.

BRIEF SUMMARY

By way of introduction, the preferred embodiments described below include methods, instructions, and systems for adaptive image optimization in induced wave ultrasound imaging. The values for various transmit and receive parameters may be set adaptively. Based on feedback from use with a given patient, the values are set to better optimize signal-to-noise ratio, off-time, tracking accuracy or other consideration. Transmit frequency, F-number, line spacing, tracking pulse repetition frequency, line sampling count, push pulse length and/or push pulse amplitude values may adapt.

In a first aspect, a method is provided for adaptive image optimization in induced wave ultrasound imaging. Acoustic energy is transmitted into a patient. A wave is generated in response to the transmitting. A region of the patient is scanned with ultrasound. From the scanning, displacement of tissue caused by the wave is detected. A transmit frequency, line spacing, F-number, pulse repetition frequency, line sampling count, acoustic energy amplitude, pulse length of the acoustic energy, or combinations thereof adapt as a function of the displacement.

In a second aspect, a non-transitory computer readable storage medium has stored therein data representing instructions executable by a programmed processor for adaptive image optimization in induced wave ultrasound imaging. The storage medium includes instructions for acoustic radiation force or shear wave imaging a region of a patient, and adapting a transmit frequency, line spacing, F-number, pulse repetition frequency, line sampling count, acoustic energy amplitude, acoustic energy pulse length, or combinations thereof of the imaging as a function of information from the imaging.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

ARFI and shear wave imaging modes are adaptively optimized for the tissue type and patient being scanned. The optimization improves the elasticity or other tissue characteristic imaging without specifically classifying the tissue being imaged. One or more of various parameters may adapt to a given patient and tissue being examined. For example, transmit frequency, line spacing, F-number, pulse repetition frequency (PRF), interleaved PRF (line sample count), and/or push pulse amplitude are adaptively optimized in radiation force imaging or in shear wave tracking.

The optimization may produce larger displacement amplitude, improved tracking signal-to-noise (SNR), image uniformity, and/or reduced cool down time than if using a configuration generic to the imaging modality and/or a generalized application. The optimization may improve the imaging even for transmit and receive configurations specific to a tissue type, but not a given patient.

The optimization may use a single instance of feedback, such as setting a parameter based on a measured displacement value. Alternatively, the optimization of the value or values may be based upon the results of iterative interrogations. Different settings are tested. A sufficient or best one of the test settings may then be selected and used. Interpolation or extrapolation may be used to calculate a value for a parameter other than a tested value. Results from sequential interrogations are interpolated or extrapolated to select a setting that is different from one of the settings used during the interrogation phase.

Adaptive optimization is applied prior to a single static image capture. The adaptive process may be performed after or while a test image is captured, but prior to acquiring an image to be used for diagnosis. Once optimization is performed, the image for diagnosis is acquired. Multiple images for diagnosis, using the same settings, may be acquired. In alternative embodiments, the optimization is repeated during real-time induced wave imaging. Periodically, in response to a trigger, or for each image, the settings or values of one or more parameters are adapted.

Figure 1:
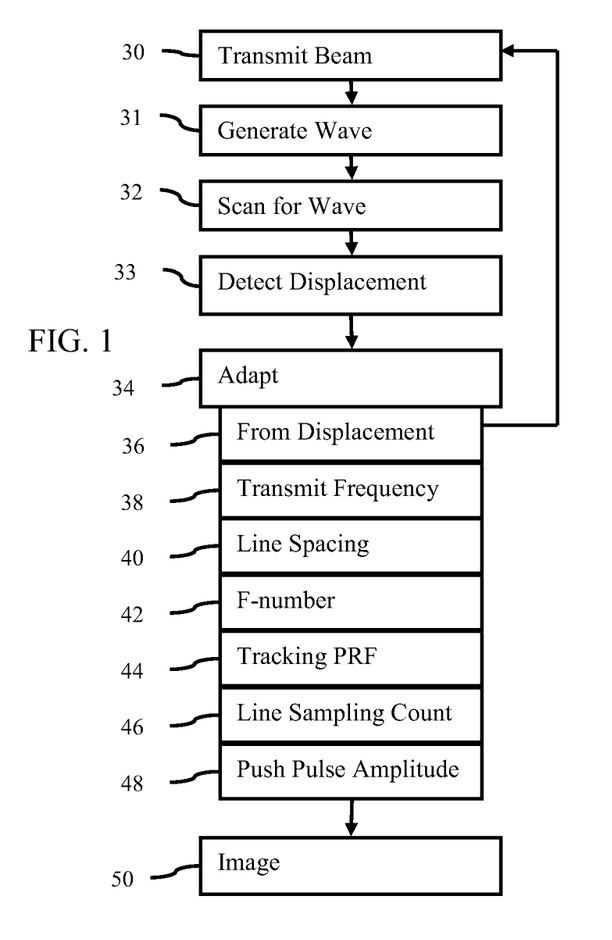
FIG. 1 is a flow chart diagram of one embodiment of a method for adaptive image optimization in induced wave ultrasound imaging.

FIG. 1 shows a method for adaptive image optimization in induced wave ultrasound imaging. The method is implemented by the system of FIG. 2 or a different system. Additional, different, or fewer acts may be provided. For example, any combination of one or more of acts 38-48 is not performed. As another example, act 30 is not performed and a source of stress for generating a wave is provided by the body, manually, using a thumper, or by another mechanism. The acts are performed in the order described or shown, but may be performed in other orders.

The method is performed for each of one or more locations. In one embodiment, the method is performed for each of B-mode or other scan sample locations in an entire field of view or a region of interest. Less or more dense sampling may be used for induced wave imaging than for B-mode or other imaging.

Acts 30-33 (transmitting, generating, scanning and detecting) correspond to induced wave imaging. Acoustic energy is used to induce a wave in a region of a patient. The acoustic energy is a pushing pulse for moving the tissue. The region is scanned to track or detect the wave. The displacement of tissue due to the wave traveling through the region indicates the presence of the wave. The timing associated with the displacement may be used to determine velocity of the wave. Other tissue characteristics may be determined from the displacement and/or velocity information, such as tissue modulus.

Different types of waves may be generated and/or tracked. Longitudinal waves are tracked for acoustic radiation force imaging, such as elastography or strain imaging. Shear waves are tracked for shear wave or shear wave velocity imaging.

In act 30 of FIG. 1, acoustic energy is transmitted into a patient. The acoustic energy acts as an impulse excitation. For example, a 400 cycle transmit waveform with power or peak amplitude levels similar or higher than B-mode transmissions for imaging tissue is transmitted. In one embodiment, the transmission is a radiation force sequence applied to the field of view. Any acoustic radiation force imaging (ARFI) sequence may be used. Any number of cycles may be used.

The transmission is configured by power, amplitude, timing or other characteristic to cause stress on tissue sufficient to displace the tissue at one or more locations. For example, a transmit focus is positioned near a bottom, center of the field of view to cause displacement throughout the field of view. The transmission may be repeated for different sub-regions.

The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient.

In act 31, a wave is generated in response to the transmission of the acoustic energy. The tissue is forced to move in the patient. The transmitted excitation causes displacement of the tissue. At the focal point or region, a longitudinal, shear or other type of wave is generated in the tissue. For example, a shear wave is generated and propagates from the focal region. As the shear wave travels through tissue, the tissue is displaced. Longitudinal waves or other causes of displacement may be used.

In act 32, a region of the patient is scanned with ultrasound. The displacement is detected with ultrasound scanning. A region, such as a region of interest, entire field of view, or sub-region of interest, is scanned with ultrasound. For a given time, ultrasound is transmitted to the tissue or region of interest. Any now known or later developed displacement imaging may be used. For example, pulses with 1-5 cycle durations are used with an intensity of less than 720 mW/cm$^2$. Pulses with other intensities may be used.

Echoes or reflections from the transmission are received. The echoes are beamformed, and the beamformed data represents one or more locations. To detect the displacement, ultrasound energy is transmitted to the tissue undergoing displacement and reflections of the energy are received. Any transmission and reception sequence may be used.

By performing the transmitting and receiving multiple times, data representing a one, two, or three-dimensional region at different times is received. The frequency of this repetition is the pulse repetition frequency. The transmission and reception are performed multiple times to determine change due to displacement. By repetitively scanning with ultrasound, the position of tissue at different times is determined.

For shear wave imaging, an impulse excitation generates a shear wave at a spatial location. Where the excitation is sufficiently strong, a shear wave is generated. The shear wave propagates through tissue more slowly than the longitudinal wave along the acoustic wave emission direction. The shear wave propagates various directions, including a direction perpendicular to the direction of the applied stress. The displacement of the shear waves is greater at locations closer to the location at which the shear wave is generated.

Ultrasound data is obtained. At least some of the ultrasound data is responsive to the shear wave. A region of interest is monitored to detect the shear wave. The region of interest is any size, such as 6 mm in lateral and 10 mm in axial. This detection region is monitored by ultrasound. For example, B-mode scans are performed to detect tissue displacement caused by the shear wave. Doppler, color flow, or other ultrasound mode may be used to monitor for the shear wave.

The monitoring is performed for any number of scan lines. For example, four receive beams are formed in response to each transmission. After transmitting the excitation to generate the wave, B-mode transmissions are performed repetitively along a single scan line and receptions along four adjacent scan lines. In other embodiments, only a single receive beam or other numbers of receive beams are formed in response to each transmission. Any number of repetitions may be used, such as about 120 times. Some of the ultrasound data, such as at the beginning or end of the repetitions, may not be responsive to the shear wave.

In act 33, displacement of tissue caused by the wave is detected in response to the scanning. The echoes are detected using B-mode or Doppler detection. The displacement is detected from the differences for each spatial location over time. For example, the velocity, variance, shift in intensity pattern (e.g., speckle tracking), or other information is detected from the received data as the displacement. For velocity based wave imaging, a displacement profile of response in the patient is determined. For example, the displacement profiles for different locations are determined.

The displacement caused by the force or stress is measured. The displacement may be measured over time at one or more locations. The displacement measurement may begin before the stress or impulse ends, such as using a different frequency or coding. Alternatively, the displacement measurement begins after the impulse ends. Since the shear, longitudinal or other wave causing the displacement in tissue spaced from the point or region of stress takes time to travel, the displacement from a relaxed or partially stressed state to a maximum displacement and then to a relaxed state may be measured. Alternatively, the displacement is measured only while the tissue is relaxing to form the maximum.

The measurement is of the amount or magnitude of the displacement. The tissue is moved in any direction. The measurement may be along the direction of greatest movement. The magnitude of the motion vector is determined. Alternatively, the measurement is along a given direction, such as perpendicular to the scan line regardless of whether the tissue is displaced more or less in other directions.

In one embodiment using B-mode data, the data from different scans is correlated. For example, a current set of data is correlated multiple times with a reference set of data. Different relative translations and/or rotations between the two data sets are performed. The location of a sub-set of data centered at a given location in the reference set is identified in the current set.

The reference is a first set of data or data from another scan. The same reference is used for the entire displacement detection or the reference data changes in an ongoing or moving window.

The correlation is one, two or three-dimensional. For example, correlation along a scan line away and toward the transducer is used. For a two dimensional scan, the translation is along two axes with or without rotation. For three dimensional scanning, the translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

As the wave propagates through the scan lines, the B-mode intensity may vary due to displacement of the tissue. For the monitored scan lines, a sequence of data is provided representing a time profile of tissue motion resulting from the wave. For example, data from a plurality of spatial locations (e.g., along the scan lines) is correlated as a function of time. Any elasticity or shear detection may be used. For each depth or spatial location, a correlation over a plurality of depths or spatial locations (e.g., kernel of 64 depths with the center depth being the point for which the profile is calculated) is performed. Two or three-dimensional displacement in space may be used. One-dimensional displacement along a direction different from the scan lines or beams may be used.

The spatial offset with the highest or sufficient correlation at a given time indicates the amount of displacement. Displacements may be determined for a given location at different times. The temporal profile for a given location indicates detection of the wave. The profile is examined for a non-noise or single instance of variation. A peak in the profile, with or without temporal low pass filtering, indicates the passing of the wave front. The greatest displacement is selected, but the average or other displacement statistic may be used. The maximum displacement at a given location is detected. Alternatively, an average or other shear is detected. In other embodiments, the displacement, whether maximum or not, at a given time (e.g., 10 milliseconds after generation or X milliseconds per unit of distance from the focal region) is used.

The displacement profile may be smoothed or filtered for the maximum calculation. In other embodiments, the raw or unfiltered displacement curve may be used. The maximum value over the entire or portion of the profile is identified or determined.

The discussion above is for one depth. The sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 for 5 mm or 400 for 10 mm.

Ultrasound data representing different locations in the region of interest is obtained. The ultrasound data is obtained in real-time with the scanning or obtained from a memory. For each location, the motion information represents the response at different times. Other scanning, monitoring, or techniques may be used to obtain ultrasound data to estimate displacement magnitude.

Shear or longitudinal velocity may be detected for the different spatial locations of the tissue. For each location, the displacement as a function of time is determined. The velocity is obtained by determining a time from generation of the wave until detection of the wave at a different location. The time and distance to the location determine the velocity. The distance is known from the scan line spacing (i.e., the transmit beam position for generating the wave and the receive beam position for detecting the wave). The time is known from the relative time between generation and detection of the wave.

Other techniques may be used to detect the peak in the profile. For example, a regression is applied. Since the wave velocity is linear, a robust linear regression with automated outlier detection may indicate the wave velocity. The ultrasound data for all of the sample points in the region of interest is plotted for distance as a function of time or by time and distance. The linear regression is applied to the plot or data, providing a line fit to the data. The slope of the line indicates the shear wave velocity.

Various aspects of the transmission, scanning, and detecting may be controlled. Values for different parameters are set. In one embodiment, the values are set based on a selected configuration. For example, the user selects shear wave or ARFI imaging. In response, predetermined parameters are loaded for operating the system. The predetermined parameters are the same for every application of that type or mode of imaging. Alternatively, further selections, such as imaging the liver or other type of tissue, for a given mode may result in configuring with different values.

Example types of parameters for which the values may be set are a transmit frequency for act 30, a transmit frequency for act 32, line spacing for act 32, F-number for act 30, F-number for act 32, pulse repetition frequency for act 30, pulse repetition frequency for act 32, line sampling count for act 30, line sampling count for act 32, acoustic energy (e.g., push pulse) amplitude for act 30, or combinations thereof. Different, additional, or fewer parameters may be set with different values.

The values of the parameters may be optimized adaptively in act 34. Using data received from scanning a given region of a given patient, the values may be adapted to better image the region. Rather than relying on predetermined values for a given scanning situation, one or more of the values may be altered to account for some aspect of the imaging. Optimization may be an improved value for one or more criteria, even if not the best value for the given criteria.

The adaptation occurs during ARFI, shear wave, or other induced wave imaging. Adaptive optimization may be applied prior to acquiring a static image or continuously during real-time imaging. For example, the values are determined using feedback from the scanning or displacement prior to presenting an image for diagnosis to the user. Subsequent images use those same settings, at least during a given examination of a patient for a sonography session. As another example, the adaptation continues or is performed at different times during the examination. Periodic or triggered adaptation may be used.

The adapting of act 34 is a function of any feedback, such as amplitude of data. In one embodiment represented in act 36, the feedback is displacement data or data derived from displacement. For example, the velocity may be derived from the displacement information. The feedback, such as displacement, is directly used. For example, a value is set based on the amount of displacement for a location or region. Alternatively, the displacement or other feedback information is used to derive a value. For example, a signal-to-noise ratio, difference in displacement, velocity, or thresholding of displacement is used to set a value.

In one embodiment, the signal-to-noise ratio of the displacement is calculated. The noise value may be measured, such as measuring an average displacement over a region when not subjected to the acoustic energy of act 30. Alternatively, the noise value is assumed or based on empirical data, such as a displacement of 1 micron or less being considered noise.

The signal level for displacement is the magnitude of the displacement. The magnitude may be along a given dimension (e.g., one dimensional magnitude) or may be from a plane or volume (e.g., two or three dimensional magnitude).

For the signal-to-noise ratio, the signal is divided by the noise. Where the noise is 1 micron, the displacement in microns is the signal-to-noise ratio. Other combinations of the signal and noise may be used. The resulting signal-to-noise ratio may be used to adapt a parameter.

In another embodiment, wave distance and/or wave velocity is calculated from the displacement. The wave distance may be a distance away from the focal region of the transmission of act 30 at which the wave is above a threshold level, such as the noise floor. For example, the wave may cause displacement of tissue greater than 1 micron over 4 mm, but not above 1 micron for greater distances. The 4 mm or other distance is measured from the displacements for the different locations. The velocity may be calculated as discussed above.

In yet another embodiment, the off-time for the transmission of act 30 is used. The displacement or other feedback information may indicate an excessive amplitude or length of transmission. Based on this excess, the acoustic power provided to the region may be reduced. Since ultrasound transmissions are limited due to transducer and tissue temperatures, the transmissions may have to cease for a period. By adapting based on the excess, the off-time may be altered to be less. Less off-time may provide for shorter cool down times. In addition to or instead of adaptively optimizing to improve SNR or shear wave tracking accuracy, cool-down time may be adaptively optimized.

The feedback or data derived from the feedback is used directly to set the value. A look-up table or calculation (e.g., applying the feedback as a variable in a function) is used to determine the value. For example, an average SNR above a threshold results in a value of X while the average SNR between the threshold and another threshold results in a value of Y. Any resolution (e.g., from binary to three or more ranges) of value setting may be used.

In another embodiment, the value is set based on a plurality of samplings. The transmitting, generating, scanning, and detecting acts 30-33 are repeated with different settings or values for one or more parameters. The feedback, such as wave amplitude, displacement amplitude, minimal cool down, wave velocity, or combinations thereof is obtained for each repetition. The setting or value associated with the sufficient or most optimum result is selected. For example, five different values are used. Of the five, the fourth value provides for the displacement magnitude to be at a desired level (e.g., above the noise floor but below on excessive level). Based on the iterative settings for the imaging, the value is selected.

The value may be interpolated or extrapolated. In the five tested values example discussed above, a curve may be fit to the feedback results. The curve may indicate an optimum value different from any of the five tested, such as value between the third and fourth value.

The value may be based on one or multiple criteria. For example, the SNR is used to set transmit frequency. As another example, both the transmit amplitude and the velocity are used to set the PRF and line sampling count.

The adaptation may be performed for each parameter sequentially. Alternatively, more than one value is altered based on the feedback at any given time. The adaptation may be iterative to obtain a combination of values for different parameters. Any matrix or other solution to the iterative approach may be used.

Acts 38-48 provide some examples of adapting. In act 38, the transmit frequency is adapted to the imaging of a given region of a patient. The transmission of act 30 is repeated at different frequencies. Alternatively, a broadband (e.g., chirp) transmission is provided with fewer or no repetitions. The transmission frequency associated with the highest or largest magnitude of displacement is selected for subsequent use. The push pulse transmit frequency is adaptively optimized by sequentially transmitting several different push pulses with different transmit frequencies and determining which transmit frequency produces the largest displacement or wave amplitude at the depths of interest. For the broadband transmission, a Fourier analysis of the displacement or other characteristic change of the profile of displacement over time may indicate a particular frequency associated with the greatest response.

In another embodiment, the transmit and/or receive frequency used for the scanning of act 32 adapts. The scanning is repeated at different scanning frequencies, such as different tracking pulse transmit frequencies (e.g., 1.5-4.5 MHz in 1 MHz increments). The transmit and/or receive frequency is different for each repetition associated with different transmissions of act 30. Within the repetitions for scanning in response to one wave, the frequency is the same. A given repetition may include multiple scans, such as associated with detecting the wave after each transmission of act 30. The same frequency is used for scanning and detecting after a given transmission of act 30, but is changed for subsequent scanning and detecting after another transmission of act 30. Alternatively, the transmit and/or receive frequency of the scanning of act 32 is changed for different scan lines or for different frames (region scans) but in response to the same wave (transmission act 30).

To adapt the scanning frequency, the displacements are detected for each repetition. The signal-to-noise ratios of the displacements are calculated. The scanning frequency associated with an optimal, such as a highest or sufficient, signal-to-noise ratio is selected for subsequent scanning. The selected frequency may be extrapolated or interpolated based on the signal-to-noise ratios of other scanning frequencies.

In act 40, the line spacing adapts. The line spacing is the density or lateral extent of the receive scan lines in the scanning of act 32. For example, samples along 4 or 16 lines are received in response to a given scanning transmission where the lines are 1 mm, 2 mm, or other distance apart. As another example, only 3 or 13 scan lines are used for receive where the distance to cover by the scanning is less. In other embodiments, the line spacing is the density of the spacing of regions or the density of the focal regions of the transmission of act 30.

In one embodiment, the line spacing adapts as a function of the wave velocity. The wave velocity is calculated from the displacement. The line spacing is denser or the scan lines are closer together for lower velocities. Waves traveling at higher speeds may be better tracked by increasing the window size or decreasing the spatial resolution. Less dense line spacing may limit or avoid overheating of the transducer and/or the tissue.

In another embodiment, the line spacing for radiation force imaging may be adaptively optimized by sequentially acquiring images or data using different line spacing. A spatial variance is calculated from the displacement information. The line spacing associated with the least amount of spatial variance in the displacement may provide the best uniformity.

In yet another embodiment, the line spacing is set for a lateral distance. The level of displacement at a given point or the range of locations for which displacement is above a threshold (e.g., the noise floor or value greater than noise) indicates a spatial extent to which detection may be expected. The lateral distance for the lines is set based on the lateral extent to which the wave may be detected. For example, the tracking pulse line spacing or number of lines for shear wave imaging may be adaptively optimized by using multiple firings to determine the largest lateral shear wave tracking distance that can be achieved and then placing the subsequent tracking lines within that maximum distance.

In act 42, the value of the F-number adapts. The F-number is controlled by the size of the aperture, spacing of the elements, apodization, delay/phase profile, or other characteristic altering the amount or size of focus. The F-number for the pushing pulse or stress transmission of act 30 is set.

The F-number adapts as a function of the displacement. Greater focus is provided for lesser displacement, and lesser focus is provided for greater displacement. A greater focus may result in a higher displacement but a smaller region for which the wave is generated in act 31. This may alter the range of the wave. For hard or stiff tissues or structure, a greater focus may be desired. For softer or more elastic tissue with a greater attenuation, a lesser focus but correspondingly larger region of wave generation may be desired.

The absolute value of a measured displacement may be used to determine the F-number, such as through a look-up table. Alternatively, acts 30-33 are repeated for different F-number settings of the acoustic energy of act 30. The F-number associated with a desired, highest, or sufficient displacement is selected.

In act 44, the pulse repetition frequency (PRF) adapts. The rate at which the scanning of act 32 is performed is set. For example, the shear wave tracking PRF is adaptively optimized. The PRF for scanning for longitudinal waves may be adaptively optimized.

The PRF adapts based on the maximum wave velocity. The maximum wave velocity is a highest velocity in the scanned region. Displacements and timing for different sample points are acquired and used to determine the maximum velocity. The maximum wave velocity dictates a sampling frequency for adequate information. The PRF is at the Nyquist frequency or higher. The Nyquist frequency is calculated from the maximum velocity. The PRF that adequately samples the maximum velocity is selected. In alternative embodiments, different PRFs are attempted and the lowest PRF associated with no aliasing is selected.

In act 46, the line sampling count adapts. If the maximum PRF cannot be achieved due to the roundtrip travel time of the tracking pulses, interleaved push pulses and offset-in-time tracking pulses at the maximum allowed or other lesser PRF may be used. To increase the sampling frequency, the line sampling count adapts. For example, a region is scanned to track the wave. Due to depth and the maximum velocity, a sufficient number of scans for a given wave may not be acquired. The line sampling count is increased by providing for a repetition of the acts 30-33 for the same region. One repetition acquires samples for the region along the receive lines at a first timing off-set from the transmission of act 30 (e.g., every 10 milliseconds starting at 5 milliseconds after the transmission of act 30 begins or ceases). Another repetition acquires samples for the same region along the same receive lines but at a different timing off-set from a subsequent transmission of act 30 (e.g., every 0 milliseconds starting at 10 milliseconds after the transmission of act 30). The data acquired from the different repetitions is interleaved together to represent acquisition at the greater frequency.

The number of repetitions or line sampling count is set based on the maximum velocity. If the maximum velocity results in a PRF that is not possible, the line sampling count is increased to provide data at the desired PRF or better, but acquired through repetition. Adapting the line sampling count may provide for better imaging or detection of high velocity shear or other waves and/or wave detection at deeper depths.

To monitor a larger region, additional receive beams are formed in response to the monitoring transmit beam (e.g., change of the line spacing). Alternatively, another wave is generated and the transmit beams and receive beams are provided at a different distance from the wave generation point. In the 6 mm×10 mm example above, 36 receive scan lines may be provided. At four receive beams per transmit beam, the process is repeated for different lateral spacing nine times. For each receive beam location, a time profile of motion information is provided, represented by the ultrasound data. Transmissions along different scan lines to monitor a same wave are avoided during formation of the temporal profile to provide higher temporal resolution, but interleaved or shifting scanning positions may be provided.

In act 48, the amplitude of the acoustic energy of the transmission of act 30 adapts. The transmitting, generating, scanning and detecting of acts 30-33 are repeated with different amplitudes for the acoustic energy of act 30. The different amplitudes cause different wave amplitudes and corresponding amounts of displacement at a given distance. Push pulse transmit amplitude is adaptively optimized by sequentially firing push pulses with different transmit amplitudes.

The push pulse amplitude that produces an adequate SNR is determined. Adequate may be above one level but below another level. Turning down the transmit voltage may reduce the cool down time between acquisitions. Alternatively, a displacement is determined without repetition and the amplitude is changed based on the displacement being above or below a desired displacement range.

In another embodiment, the pulse length of the push pulse or acoustic energy transmitted in act 30 adapts. Longer pulses generally provide for a greater amount of push or stress. Greater displacement may be caused by longer pulses, at least along a range of possible pulse lengths. The longer pulses correspond to a greater number of cycles, such as 100 cycles instead of 50 cycles. The greater length may result in more heating and/or a longer cool down time. The pulse length may adapt to the amount of displacement such that sufficient displacement is provided without excess.

Combinations of any two or more of acts 38-48 may be provided. The combinations of different possible values may be determined iteratively. Different combinations are attempted and the trends in the feedback may be analyzed to determine a next possible combination. Alternatively, the value for each parameter is determined in sequence. A priority may be assigned to any parameter so that the parameter is adapted first or last.

In act 50, induced wave imaging is performed. The imaging is performed based on the optimized values of the parameters. Using the optimized values of the parameters with or without other predetermined values or user set values, acts 30-33 are repeated to determine the wave information, such as velocity, displacement, or tissue characteristic (e.g., modulus). An image or sequence of images is generated to display the wave information. Any shear or ARFI imaging may be used.

The wave information is used for a color overlay or other modulation of display values. Color, brightness, luminance, hue, or other characteristic is modulated as a function of the displacement. For example, wave information is displayed over or with B-mode information. The displacement data is in a display format or may be scan converted into a display format. The displacement data is color or gray scale data, but may be data prior to mapping with gray scale or color scale. The information may be mapped linearly or non-linearly to the display values.

The image represents the displacement information, such as shear or moduli (e.g., the shear moduli) for the different locations. Where the values are determined for all of the grid points in a region of interest or field of view, the pixels of the display represent the wave information for that region. The display grid may be different from the scan grid and/or grid for which displacements are calculated. Scan conversion, nearest neighbor selection, interpolation and/or extrapolation may be used to conform the wave information resolution to the display resolution.

The image may include other data. For example, B-mode or other data representing tissue, fluid, or contrast agents in the same region is included. The displacement data is used for an overlay of or combination with the other data. The other data assists the user in determining the location of the beam relative to the tissue to be treated.

Figure 2:
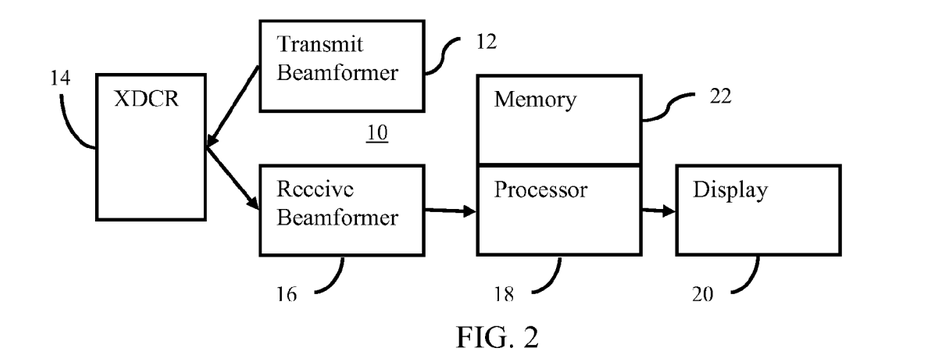
FIG. 2 is a block diagram of one embodiment of a system for adaptive image optimization in induced wave ultrasound imaging.

FIG. 2 shows one embodiment of a system 10 for adaptive optimization of induced wave imaging. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system.

The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waveforms, one or more beams are formed. A sequence of transmit beams are generated to scan a two or three-dimensional region. Sector, Vector®, linear, or other scan formats may be used. The same region is scanned multiple times. For flow or Doppler imaging and for induced wave imaging, a sequence of scans is used. In Doppler imaging, the sequence may include multiple beams along a same scan line before scanning an adjacent scan line. For induced wave imaging, scan or frame interleaving may be used (i.e., scan the entire region before scanning again). In alternative embodiments, the transmit beamformer 12 generates a plane wave or diverging wave for more rapid scanning.

The same transmit beamformer 12 generates impulse excitations or electrical waveforms for generating acoustic energy to cause displacement. In alternative embodiments, a different transmit beamformer is provided for generating the impulse excitation. The transmit beamformer 12 causes the transducer 14 to generate high intensity focused ultrasound waveforms.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event provides a pulse of ultrasound energy for displacing the tissue. The pulse is an impulse excitation. Impulse excitation includes waveforms with many cycles (e.g., 500 cycles) but that occurs in a relatively short time to cause tissue displacement over a longer time.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band. The receive beamformer 16 may isolate information at the fundamental or transmit frequencies.

In coordination with the transmit beamformer 12, the receive beamformer 16 generates data representing the region at different times. After the acoustic impulse excitation, the receive beamformer 16 generates beams representing different lines or locations at different times. By scanning the region of interest with ultrasound, data (e.g., beamformed samples) is generated.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for displacement. Alternatively, the B-mode data is also used to determine displacement. As another example, data for displacement-based classification and induced wave imaging is performed with a series of shared scans and B-mode or Doppler scanning is performed separately or using some of the same data.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples. In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement and calculating displacement profile properties. For example, the separate processor is configured by hardware and/or software to perform any combination of one or more of the acts shown in FIG. 1.

The processor 18 is configured to estimate tissue displacement induced by the acoustic impulse excitation. Using correlation, tracking, motion detection, or other displacement measuring, the amount of shift in position of the tissue is estimated. The estimation is performed multiple times through a period, such as from prior to the tissue moving due to the impulse to after the tissue has mostly or completely returned to a relaxed state (e.g., recovered from the stress caused by the impulse excitation).

The processor 18 may derive at least one parameter describing a characteristic of the tissue and/or the displacement. For example, the signal-to-noise ratio of the displacement is derived. As another example, the maximum displacement of the displacement and/or velocity is derived. The processor 18 may calculate other parameters, such as a distance, cool-down, or off time. Using the displacement or other detected information, the values of one or more parameters is determined by the processor 18 or other controller. Any transmit, receive, or scanning parameter may adapt to the scanned region based on feedback.

The processor 18 may be configured to classify tissue in the region. Tissue may be fluid tissue or solid tissue. The classification may be between types of tissue, between tissue and fluid, or between types of tissue and one or more other classes. In one embodiment, the processor 18 classifies the material at a location as fluid/fluid tissue, solid tissue, and other/non-determinative.

The processor 18 operates pursuant to instructions stored in the memory 22 or another memory for adaptive image optimization in induced wave ultrasound imaging. The processor 18 is programmed for providing feedback for adapting shear or ARFI imaging. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 is configured by the processor 18 or other device by input of the signals to be displayed as an image. The display 20 displays an image representing shear, elasticity, or other wave information for different locations in a region of interest or an entire image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for adaptive image optimization in induced wave ultrasound imaging, the method comprising:
    transmitting, from a transducer of an ultrasound system, acoustic energy into a patient;
    generating a wave in response to the transmitting;
    scanning, with a beamformer of the ultrasound system, a region of the patient with ultrasound;
    detecting, from the scanning, displacement of tissue caused by the wave; and
    changing a transmit setting of the ultrasound system for transmit operation subsequent to the transmitting, the transmit setting being for a transmit frequency, line spacing, F-number, pulse repetition frequency, line sampling count, acoustic energy amplitude, acoustic energy pulse length, or combinations thereof and the transmit setting changing to a value that is a function of the displacement.

2. The method of claim 1 wherein the wave comprises a longitudinal wave, and the acts of transmitting, generating, scanning and detecting being performed as acoustic radiation force imaging.

3. The method of claim 1 wherein the wave comprises a shear wave, and the acts of transmitting, generating, scanning and detecting being performed as shear wave imaging.

4. The method of claim 1 wherein changing to the value that is the function of the displacement comprises:
    calculating a signal-to-noise ratio of the displacement; and
    adapting the transmit setting as a function of the signal-to-noise ratio.

5. The method of claim 4 wherein calculating the signal-to-noise ratio comprises calculating a magnitude of the displacement and dividing the magnitude by a value of one for the noise.

6. The method of claim 1 wherein changing to the value that is the function of the displacement comprises:
    calculating a wave distance or wave velocity from the displacement; and
    adapting the transmit setting as a function of the wave distance or wave velocity.

7. The method of claim 1 wherein changing further comprises adapting the transmit setting as a function of off time of the transmitting, the off time being a limitation due to transducer or tissue temperature.

8. The method of claim 1 wherein changing comprises:
performing the transmitting, generating, scanning, and detecting with a first value of the transmit setting;
repeating the transmitting, generating, scanning, and detecting with different values of the setting; and
selecting the value as one of the values for the setting.

9. The method of claim 1 wherein changing comprises:
performing the transmitting, generating, scanning, and detecting with a first value of the transmit frequency;
repeating the transmitting at different values of the transmit frequency;
setting the value of the transmit frequency of the acoustic energy as a function of a highest of the displacements caused by the performance and repetition at the different values of the transmit frequency.

10. The method of claim 1 wherein changing comprises:
performing the scanning with a first value of a scanning frequency;
repeating the scanning at different values of the scanning frequency;
calculating signal-to-noise ratios from the displacements detected from the performing and repeating of the scanning; and
setting the transmit frequency of the scanning as a function of the signal-to-noise ratios.

11. The method of claim 1 wherein changing comprises:
calculating a shear wave velocity as a function of the displacement;
setting a line spacing as a line density for the scanning, the line spacing being a function of the shear wave velocity.

12. The method of claim 1 wherein changing comprises setting the line spacing for a lateral distance, the lateral distance being a function of the displacement.

13. The method of claim 1 wherein changing comprises setting the F-number as a function of the displacement such that greater focus is provided for lesser displacement and lesser focus is provided for greater displacement.

14. The method of claim 1 wherein changing comprises:
calculating a maximum wave velocity; and
setting the pulse repetition frequency of the scanning as a function of the maximum velocity.

15. The method of claim 14 wherein setting comprises setting the pulse repetition frequency and the line sampling count as a function of the maximum velocity, the line sampling count being a number of repetitions of the transmitting, generating, scanning and detecting for each scan line.

16. The method of claim 1 wherein changing comprises:
performing the transmitting, generating, scanning, and detecting with a first value of the acoustic energy amplitude;
repeating the transmitting, generating, scanning and detecting with different values of the acoustic energy amplitude for the acoustic energy; and
setting the acoustic energy amplitude as a function of the displacements caused by the different values.

17. The method of claim 1 wherein changing further comprises interpolating or extrapolating a setting.

* * * * *